United States Patent
Nguyen et al.

(10) Patent No.: US 9,119,914 B2
(45) Date of Patent: Sep. 1, 2015

(54) METHODS FOR AUTOMATED BLOOD PRIME

(71) Applicant: Fenwal, Inc., Lake Zurich, IL (US)

(72) Inventors: Lan T. Nguyen, Vernon Hills, IL (US); John T. Foley, Wheeling, IL (US); Jonathan Prendergast, Palatine, IL (US); Matthew Schoonover, Sugar Grove, IL (US)

(73) Assignee: Fenwal, Inc., Lake Zurich, IL (US)

(*) Notice: Subject to any disclaimer, the term of this patent is extended or adjusted under 35 U.S.C. 154(b) by 313 days.

(21) Appl. No.: 13/778,474

(22) Filed: Feb. 27, 2013

(65) Prior Publication Data

US 2014/0069868 A1  Mar. 13, 2014

Related U.S. Application Data

(60) Provisional application No. 61/681,734, filed on Aug. 10, 2012.

(51) Int. Cl.
| | |
|---|---|
| *A61M 1/16* | (2006.01) |
| *A61M 1/36* | (2006.01) |
| *A61M 1/34* | (2006.01) |
| *A61M 1/30* | (2006.01) |

(52) U.S. Cl.
CPC ............. *A61M 1/16* (2013.01); *A61M 1/3609* (2014.02); *A61M 1/3643* (2013.01); *A61M 1/30* (2013.01); *A61M 1/3496* (2013.01); *A61M 2202/0429* (2013.01); *A61M 2205/12* (2013.01); *A61M 2240/00* (2013.01)

(58) Field of Classification Search
CPC ....... A61M 1/16; A61M 1/30; A61M 1/3496; A61M 1/3609; A61M 1/3643; A61M 2202/0429; A61M 2205/12; A61M 2240/00

USPC .................................................. 210/196, 650
See application file for complete search history.

(56) References Cited

U.S. PATENT DOCUMENTS

| 6,902,539 B2 | 6/2005 | Bainbridge et al. |
| 2002/0033370 A1 | 3/2002 | Bainbridge et al. |
| 2009/0211987 A1 | 8/2009 | Min |

FOREIGN PATENT DOCUMENTS

EP  2465555 A1  6/2012

OTHER PUBLICATIONS

European Search Report dated Jul. 10, 2014 for Application No. EP13178666.7 in the name of Fenwal, Inc. from the European Patent Office, Munich, Germany.
CaridianBCT; Helpful Hints for Performing a Blood Prime; CaridianBCT; Copyright 2008.

*Primary Examiner* — Dirk Bass
(74) *Attorney, Agent, or Firm* — Cook Alex Ltd.

(57) ABSTRACT

A method is disclosed for priming a kit for use in a therapeutic apheresis procedure with previously-collected blood prior to flowing the patient's whole blood into the inlet line of the kit, as part of a procedure in which a selected blood component is separated from a patient's whole blood, and replaced with a previously-collected blood component. The operator enters into the controller of the separation device the hematocrit value of the previously-collected blood. Then, in response to prompts by the controller, the operator enters a target hematocrit value for the previously-collected blood and an identification of the portion of the kit to be primed. The identified portion of the kit is automatically primed with the previously-collected blood. The patient is then connected to the inlet line of the kit in response to a prompt from the controller and the therapeutic procedure is commenced.

20 Claims, 7 Drawing Sheets

METHODS FOR AUTOMATED BLOOD PRIME

FIELD OF THE DISCLOSURE

The present disclosure relates to apheresis procedures and, more particularly, to therapeutic apheresis procedures in which a durable separation device and single-use kit are utilized and in which the kit or a selected portion thereof is primed with blood prior to use.

BACKGROUND

When performing an apheresis procedure, a single-use kit is primed prior to commencement of the procedure to remove air from the kit that might otherwise be returned to the patient/donor. This initial priming is typically done with a saline solution or a mixture of saline and anticoagulant, and at least a portion of the saline prime is typically returned to the patient/donor at the commencement of the procedure. However, when the extracorporeal blood path volume of the single-use kit is large relative to the volume of blood of the patient (for example, greater than about 10-15% of the patient's total blood volume, as may occur for pediatric or small-sized patients), or if the patient is anemic or hemodynamically unstable, the return of the saline prime at the commencement of the apheresis procedure could be detrimental to the patient's well-being.

In such instances, and more particularly in a therapeutic apheresis procedure, it may be desirable to perform a "blood prime" in which whole blood or normalized whole blood (packed red blood cells reconstituted with saline and/or albumin) is used to prime the system subsequent to the initial priming with saline so that, at the commencement of the therapeutic procedure, patient-compatible blood is returned to the patient simultaneously with blood being withdrawn from the patient, thus maintaining a generally constant total blood volume and red blood cell mass and/or volume for the patient.

In typical apheresis procedures, blood primes are performed manually by the operator with reference to an instruction sheet. Patients for whom a blood prime may be indicated are generally much more sensitive to minor shifts in their fluid balance and blood volume, and the operator must be alert to this. If the operator is inexperienced with blood priming, additional stress may result from performing the blood prime, and the operator's attention may be diverted from the monitoring of the patient. By way of the present disclosure, an automated blood prime method is provided.

SUMMARY OF THE DISCLOSURE

The present subject matter has a number of aspects which may be used in various combinations, and a disclosure of one or more specific embodiments is for the purpose of disclosure and description, and not limitation. This summary highlights only a few of the aspects of this subject matter, and additional aspects are disclosed in the drawings and the more detailed description that follows.

By way of the present disclosure, a method is provided for priming a system in which the priming fluid is previously-collected whole blood or blood product for performing a therapeutic procedure in which a selected blood component is separated from a patient's whole blood and replaced with a previously-collected blood component. The procedure utilizes a durable separation device and a single-use kit, with the kit comprising an inlet line, separation chamber, a replacement fluid line (if required for the procedure), and a return pathway, and a durable separation device comprising a programmable controller including a user interface, wherein the priming of at least a portion of the kit with previously-collected blood or blood product is performed prior to flowing the patient's whole blood into the inlet line of the kit.

In one aspect of the disclosure, the priming method comprises: entering into the controller in response to a prompt by the controller the hematocrit value of the previously-collected blood or blood product; entering into the controller in response to a prompt by the controller a target hematocrit value for the previously-collected blood or blood product when residing in the kit; entering into the controller in response to a prompt by the controller an identification of the portion of the kit to be primed with the previously-collected blood or blood product; automatically priming the identified portion of the kit with the previously-collected blood or blood product; connecting the patient to the inlet line and return pathway of the kit in response to a prompt from the controller after completion of the selected priming; and commencing with the therapeutic procedure, including, but not limited to, tracking fluid balance and hematocrit of the patient accounting for the volume of previously collected blood or blood product used for priming.

In another aspect of the disclosure, the method comprises priming either the entire kit or the return pathway.

In a further aspect of the disclosure, the method comprises connecting the source of the previously-collected blood or blood product to the inlet line of the kit and a waste bag to the return line in response to a prompt by the controller after selecting priming the entire kit.

In another aspect of the disclosure, the method comprises priming the entire kit with saline prior to priming either the entire kit or the return pathway with the previously-collected blood or blood product.

In a further aspect of the disclosure, the method comprises connecting a source of the previously-collected blood or blood product to the replacement fluid line and a waste bag to the return line in response to a prompt by the controller after selecting priming the return pathway, weighing the source of the previously-collected blood or blood product, and diverting fluid displaced by the priming of the return pathway to the waste bag.

In another aspect of the disclosure, the method comprises determining the hematocrit value for the whole blood of the patient and entering into the controller that hematocrit value for the target hematocrit value, and adding saline to the previously-collected blood or blood product during priming in an amount sufficient to attain the target hematocrit, if the target hematocrit value is less than the hematocrit of the previously-collected blood or blood product.

In another aspect of the disclosure, the method comprises diverting the fluid displaced by priming of the entire kit to the patient.

BRIEF DESCRIPTION OF THE DRAWINGS

These and other aspects of the present subject matter are described in the following detailed description and shown in the attached figures, in which.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
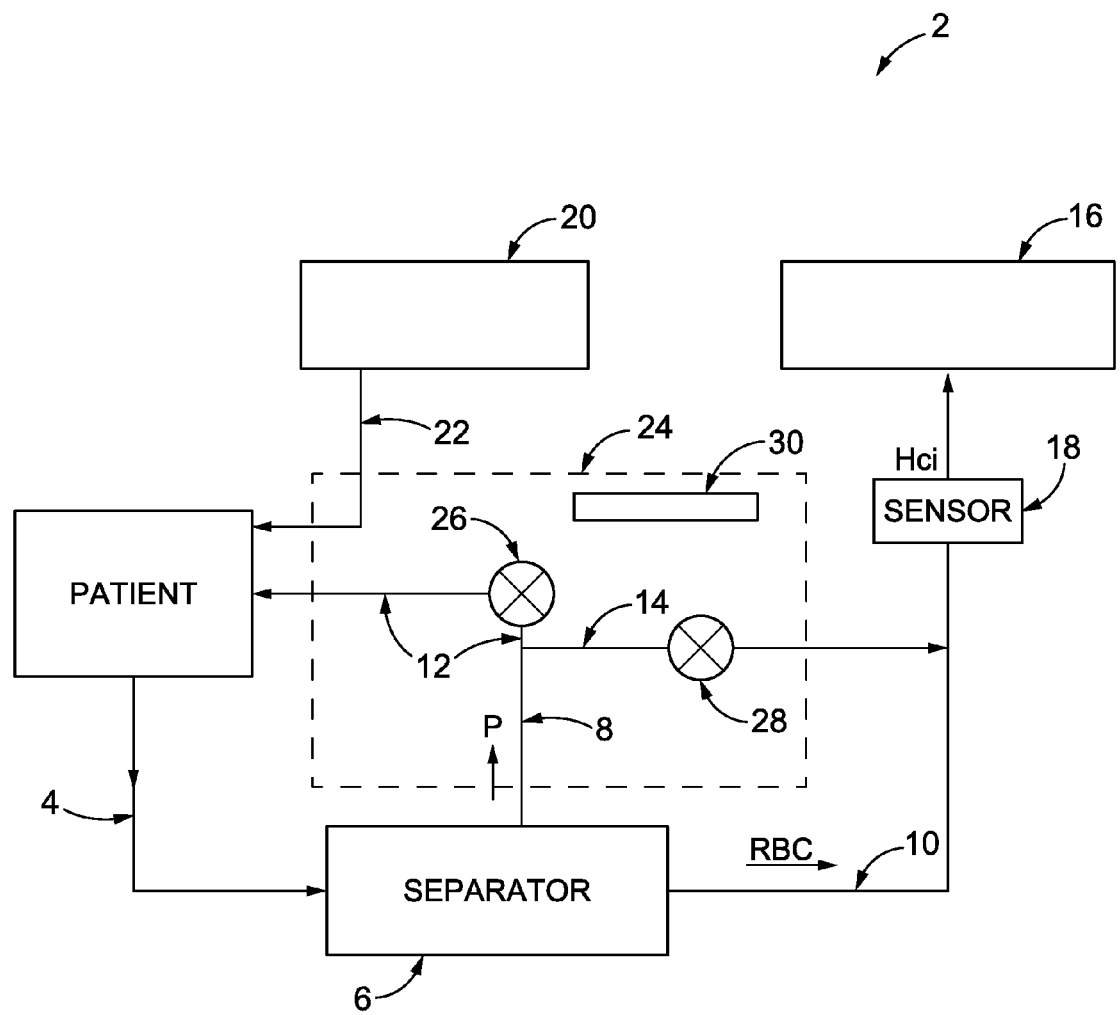
FIG. 1 a diagrammatic view of a system for performing a method in accordance with one embodiment of the subject matter described herein.

In accordance with one embodiment of the present disclosure, FIG. 1 schematically illustrates a processing system, generally indicated at 2, that may be used for a therapeutic apheresis procedure in accordance with the subject matter described herein. The system 2 is particularly well suited to processing whole blood and/or other suspensions of biological fluids. By way of example and not limitation, the systems and methods described herein are particularly suited for a therapeutic red blood cell exchange procedure, therapeutic plasma exchange procedures, and mononuclear cell (MNC) collection, during which the selected blood component is separated from the whole blood withdrawn from the patient and the remaining blood components, replacement cells and/or other replacement fluids, are returned to a patient. It is understood that the systems described herein are not limited to such collection and exchange procedures and that other procedures are also possible.

In FIG. 1, the system 2 includes a first flow path, generally indicated at 4, that communicates with a patient for flowing (withdrawing) at least a first fluid, such as whole blood, from the patient. In FIG. 1, a separator, generally indicated at 6, may be associated with the first flow path 4 for receiving the whole blood and separating the whole blood from the patient into one or more separated blood components. By way of example and in the context of a red blood cell exchange procedure, the separator 6 may separate primarily red blood cells from plasma and preferably separates red bloods cells from the remaining blood components, e.g., plasma, platelets and white blood cells. In FIG. 1, a second or plasma flow path, generally indicated at 8, preferably communicates with the separator 6 for flowing the separated plasma and/or other remaining blood components, such as platelets and/or white blood cells, from the separator 6. A third or red blood cell flow path, generally indicated at 10, preferably communicates with the separator 6 for flowing the separated red blood cells from the separator.

The separated plasma may flow from the separator 6 generally in two ways or along two branches of the second flow path 8, such branches generally indicated at 12 and 14. A first branch 12 may communicate, either directly or indirectly with the patient and a second branch 14 may communicate with the red blood cell flow path 10 at a selected location to combine and/or mix with the separated red blood cells.

Also in FIG. 1, a first container or reservoir, generally indicated at 16, is preferably associated with the red blood cell flow path 10, such as at a downstream end of such flow path 10. The first reservoir 16 preferably communicates with the separator 6 to allow the separated red blood cells to flow from the separator 6 to such reservoir 16. A monitoring device, such as a sensor, generally indicated at 18, is optionally associated with the third flow path 10 at a sensing location that is preferably downstream of the selected location where separated plasma in flow path 14 and red blood cells in flow path 10 may combine.

In FIG. 1, a second reservoir, generally indicated at 20, may be associated with a source of a replacement fluid, such as fresh red blood cells, and may communicate with the patient, either directly or indirectly, by way of a replacement fluid flow path, generally indicated at 22. While only a single reservoir containing replacement fluid is shown in FIG. 1, the system may advantageously include additional reservoirs containing replacement fluid, as will be described in greater detail below. Although in FIG. 1, the replacement red blood cells flow to the patient separately from the separated plasma, it is also possible for the replacement red blood cells and separated plasma to flow by way of a combined flow path that communicates either directly or indirectly with the patient. As a further option, the system may include a hematocrit sensor.

In FIG. 1, a controller or flow controller, generally indicated at 24, is preferably associated with one or more flow controlling devices, such as, for example, valves, generally indicated at 26 and 28, that preferably control the addition of the separated plasma to the separated red blood cells. In FIG. 1, such valves 26 and 28 are preferably respectively associated with the first and second branches 12 and 14 of the plasma flow path 8 for respectively controlling fluid flow of the separated plasma either to the patient or to the red blood cell flow path 10. By way of example, when the valve 26 is open and the valve 28 is closed, the separated plasma is directed to the patient. Alternatively, when the valve 26 is closed and the valve 28 is opened, the separated plasma is directed to the separated red blood cells in the red blood cells flow path 10. As a further alternative, the plasma flow path 8 may be provided with a pump (not shown in FIG. 1) to control the amount of plasma flowing to either the patient or to the red blood cell flow path 10. Other types of flow controlling devices may also be used as controllers, including but not limited to pumps, such as peristaltic or diaphragm pumps, as well as gravity-controlled flow controllers. The controller 24 may also be associated with the replacement fluid flow path 22 for controlling the fluid flow of the replacement fluid and may include various pumps, valves or other similar structures for controlling such flow.

In FIG. 1, such controller 24 may include a main controller, generally indicated at 30, such as a programmable controller employing a programmable microprocessor, operatively associated with the first and second valves 26 and 28 to control the fluid flow through each valve. In accordance with the present disclosure, the controller is programmed or configured to operate the system to perform a therapeutic exchange procedure, and to optionally perform a blood prime of the flow path of the single-use fluid processing set, as set forth in greater detail below.

Figure 2:
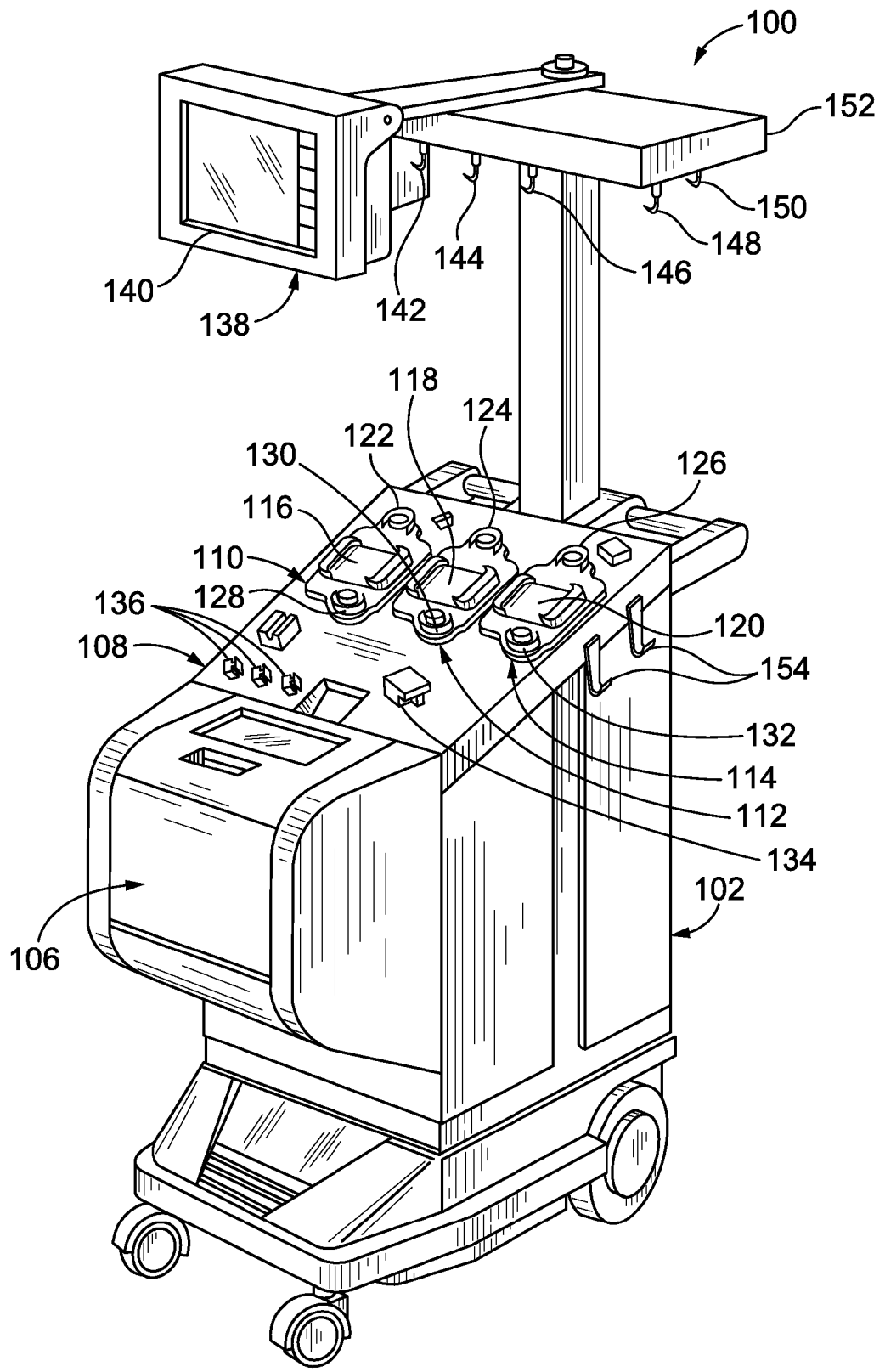
FIG. 2 is a perspective view of a reusable blood processing device that may be employed as part of or in association with the subject matter described herein.

FIG. 2 illustrates a centrifugal processing device, generally indicated at 100, that may be used for processing various fluids in accordance with the method and systems described herein. The illustrated embodiment is substantially identical to a commercial centrifuge sold by Fenwal, Inc. as the Amicus® separator, which is disclosed in numerous patents and patent applications, not limited to but including U.S. Pat. No. 5,868,696, to Giesler et al., issued Feb. 9, 1999, which is incorporated herein by reference.

As shown in FIG. 2, the centrifugal processing device 100 includes a separation assembly, specifically a centrifuge rotor assembly, generally within the housing indicated at 102, and is configured to control fluid flow through a disposable fluid processing set or kit, (generally indicated 104 in FIG. 3), used in association with the processing device 100. The separation assembly need not be a centrifugal processing assembly, and other separation technology or devices, such as membrane separators including spinning membrane separators, may also be used. The separation assembly 102 receives and separates a biological fluid, such as whole blood and/or other biological fluids, into two or more constituent components. The separation assembly 102 is preferably adapted to be durable and reusable over a long term. The fluid processing set 104, in contrast, is disposable, and a fresh sterile set is assembled with the separation assembly 102 for each use.

In FIG. 2, the separation assembly 102 includes an access compartment, generally indicated at 106, which houses a portion of the disposable set 104, such that when the separation assembly 102 is activated, the constituent components are separated within such portion of the set 104. A panel, generally indicated at 108, provides a surface for receiving another portion of the disposable set 104. For example, the panel 108 includes three pumping and valving stations, or respective left, middle and right stations, generally indicated at 110, 112 and 114, in FIG. 2, and each station 110, 112 and 114 respectively includes a valve interface portion 116, 118 and 120, that controls the opening and closing of associated valves in a disposable flow control cassette, described further below. Each station also has a respective upper flow controlling device or pump 122, 124, 126 and a lower flow controlling device or pump 128, 130, 132. Each illustrated pump 122, 124, 126, 128, 130, 132 is a peristaltic pump adapted to be associated with a section of tubing to provide flow control, although other types of pumps or other flow controlling devices, such as diaphragm pumps or gravity controlled devices are also possible. The panel 108 may further include a detector 134, such as an optical detector, and/or other sensors or clamps, generally indicated at 136, for controlling and/or monitoring fluid and/or air flow in the disposable set 104.

As shown in FIG. 2, the system 100 further includes a controller, generally indicated at 138. The controller 138 is preferably a programmable controller that is operable to control the system 100 for various processes, including a blood prime of the flow path of the processing kit, as described in greater detail below. An operator interface module 140 may allow for viewing of the past, current and/or upcoming operations and/or provide for operator input by way of a touch screen and/or one or more tactile controls. One or more weight scales 142, 144, 146, 148, 150 may be associated with the controller 138. Such scales may be attached to a platform or stand 152 that allows one or more fluid containers to be attached to or hung from the scales and to allow for weight measurement of such containers during and/or after the processing procedure. One or more hooks 154 may also extend downwardly from a right or left side of the panel 108 to allow attachment of other fluid containers and may also be associated with a weight scale, if desired.

FIGS. 3-6 illustrate one possible disposable fluid processing set 104 that may be employed for use with a fluid separation device for performing a therapeutic red blood cell exchange procedure and, more specifically, a blood prime in accordance with the present disclosure. FIGS. 3-6 differ from one another in that they illustrate the operation of the system during different stages of the described partial kit and full kit blood prime procedures.

The disposable set 104 is preferably adapted to be loaded onto a separation assembly, such as shown in FIG. 2 and disclosed in U.S. Pat. No. 5,868,696, incorporated by reference above, although other separation assemblies are also possible. The illustrated set 104 includes a double needle (one for withdrawal of fluid from a patient and one for return of fluid to the patient) processing assembly, although it is understood that the present disclosure is not limited to double needle processing and may include single needle and other types of processing sets.

The set 104 includes a draw tubing 156 and a return tubing 158 (each having a patient access device such as a needle associated therewith), a processing chamber 160, left, middle and right pumping, flow control and valving cassettes 162, 164, 166, an auxiliary reservoir or container 168 for pressure relief or for diverted air, containers 170A, 170B for replacement fluids (such as saline, albumin and/or replacement red blood cells), a container 172 for an anticoagulant, containers 174A and 174B for waste, and a container 176 for saline. Each container 170A, 170B, 172, 174A, and 176 may be respectively associated with a corresponding weight scale (see, e.g., weight scales 142, 144, 146, 148, 150 shown in FIG. 2) for determining the amount of fluid that is removed from or added to such container. The set 104 also includes various tubing paths discussed in further detail below.

Each cassette 162, 164 and 166 has a similar internal construction and, as such, only one cassette 162 will be described. However, it is understood that like alpha-numeric reference characters used in connection with cassette 162 are also applicable to cassettes 164 and 166. The left cassette 162 includes at least one and preferably a plurality of pressure sensing chambers, such as PS1, PS2, PS9, and PS10, preformed fluid flow pathways and at least one, and preferably a plurality of, valves, such as V1, V2, V3, V4, V5, V6, V7, V8, V9, and V10. The number and configuration of such chambers and valves are not limited to that shown, and other variations are also possible, including variations for the interconnecting flow paths between such chambers and valves. Each of the chambers and valves preferably is associated with a respective portion of the respective pumping and valving station 110, 112 and 114 (shown in FIG. 2) to control the flow of fluid.

As described above, each pump 122, 124, 126, 128, 130 and 132 may be a peristaltic pump adapted to be associated with a section of tubing to provide flow control. For example, each pump 122, 124, 126, 128, 130, and 132 may be associated with a respective tubing segment 178, 180, 182, 184, 186 and 188. The upper pumps 122, 124 and 126 are each associated with two pressure sensing chambers PS1 and PS2 with one being located downstream and the other located upstream of the pumps, depending on which direction is the desired flow direction, which direction may change, if desired, one or more times during and/or after the procedure. Similarly, the lower pumps 128, 130 and 132 are each associated with two pressure sensing chambers PS9 and PS10 located on either upstream or downstream side thereof. Such peristaltic pumps 122, 124, 126, 128, 130 and 132 are typically operated by rotation and include one or more outward extensions, rollers or the like that act on the exterior of the respective tubing segment 178, 180, 182, 184, 186 and 188 to progressively compress or "push" fluid in the desired direction of flow.

The set 104 further includes a first flow path 190 that fluidly communicates with the draw tubing 156 for withdrawing whole blood from a patient. An anticoagulant flow path 192 may communicate with the first flow path 190 at a Y-branch connector 194 to allow anticoagulant to mix with the whole blood as it is withdrawn from the patient/donor. Anticoagulant from the anticoagulant container 172 may be pumped to the first flow path 190 by the upper or anticoagulant pump 124 of middle cassette 164 and flow through open valves V3 and V6 of such cassette to mix with the withdrawn whole blood. The set 104 includes return or replacement fluid flow paths 214A and/or 214B that fluidly communicate with the return tubing 196 to allow one or more fluids, such as a replacement fluid, to flow to the patient. One or more saline flow paths 198 and 200 may also be in respective communication with the whole blood and return flow paths 190 and 196 to allow saline flow, if desired, before, during and/or after the procedure.

Before turning to a discussion of the method of priming the system with blood that is the subject of the present disclosure, set forth below is a brief summary of a representative red blood cell exchange procedure. By way of example and not limitation, in a red blood cell exchange procedure, the withdrawn whole blood flows into the first flow path 190 and through the left cassette 162 and the lower or whole blood pump 128 of such cassette. The first flow path 190 preferably communicates with the processing chamber 160 so as to allow the withdrawn whole blood from the patient to be separated into selected constituent blood components, such as red blood cells, platelets and/or plasma.

Outlet flow paths 202 and 208 may allow separated blood components, such as red blood cells, plasma and/or platelets, to separately exit the processing chamber 160. For example, separated red blood cells from the processing chamber 160 may flow through a red blood cell path 208. Separated plasma from the processing chamber 160 may flow through the plasma flow path 202. An optical detector, such as the optical detector 134 discussed above, may be associated with the plasma flow path 202 to assist in optical detection of blood components, e.g. platelets or red cells, in the plasma constituent.

Separated red blood cells flowing from the processing chamber 160 preferably flow through the red blood cell flow path 208 to one of the red blood cell containers 174A or 174B. Separated red blood cells may flow through the right cassette 166 into one of the containers 174A or 174B. Separated plasma preferably is pumped by operation of the lower pump 132 of the right cassette 166. Such plasma pump 132 may be employed to determine the amount of plasma that is returned to the patient and the amount of plasma that flows out with the red blood cells in flow path 208. As discussed above, the removed red blood cell containers 174A, 1748 may also be associated with weight scales for measuring the amount of the separated red blood cells (which may be combined with plasma) flowing into such containers during the procedure.

The separated plasma from the processing chamber 160 flows through the plasma flow path 202 and is returned to the patient. For example, the separated plasma may flow from the processing chamber 160 through the right cassette 166 to a first passageway 210 in communication with the return flow path 196. Separated plasma is preferably pumped by the lower or plasma pump 132. Separated plasma may flow into the return flow path 196 at a selected location or connector 212, which combines the plasma and replacement fluid into a combined fluid stream for return to the patient. The amount of plasma returned to the patient depends on the desired ending hematocrit for the patient, the patient's hematocrit, and the hematocrit of the replacement fluid blood.

Replacement fluid flows from one of the replacement fluid containers 170A, 170B to the patient through the return flow path 196. For example, the replacement fluid flows from either container 170A or 170B through a replacement fluid source path 214A or 214B to the middle cassette 164. The lower or replacement pump 130 may assist the flow of the replacement fluid. The replacement fluid flows into the return flow path 196 and flows to the patient. As noted above, separated plasma may be combined with the replacement fluid in a single fluid stream. The return flow path 196 may also flow through the left cassette 162. A combined fluid stream may also be pumped by operation of the upper left or return pump 122 to assist the return flow to the patient. However, in a double needle procedure, the pump 122 is in a flow-through mode, and return blood flows through the open pathway.

Performance of the Method

Figure 7:
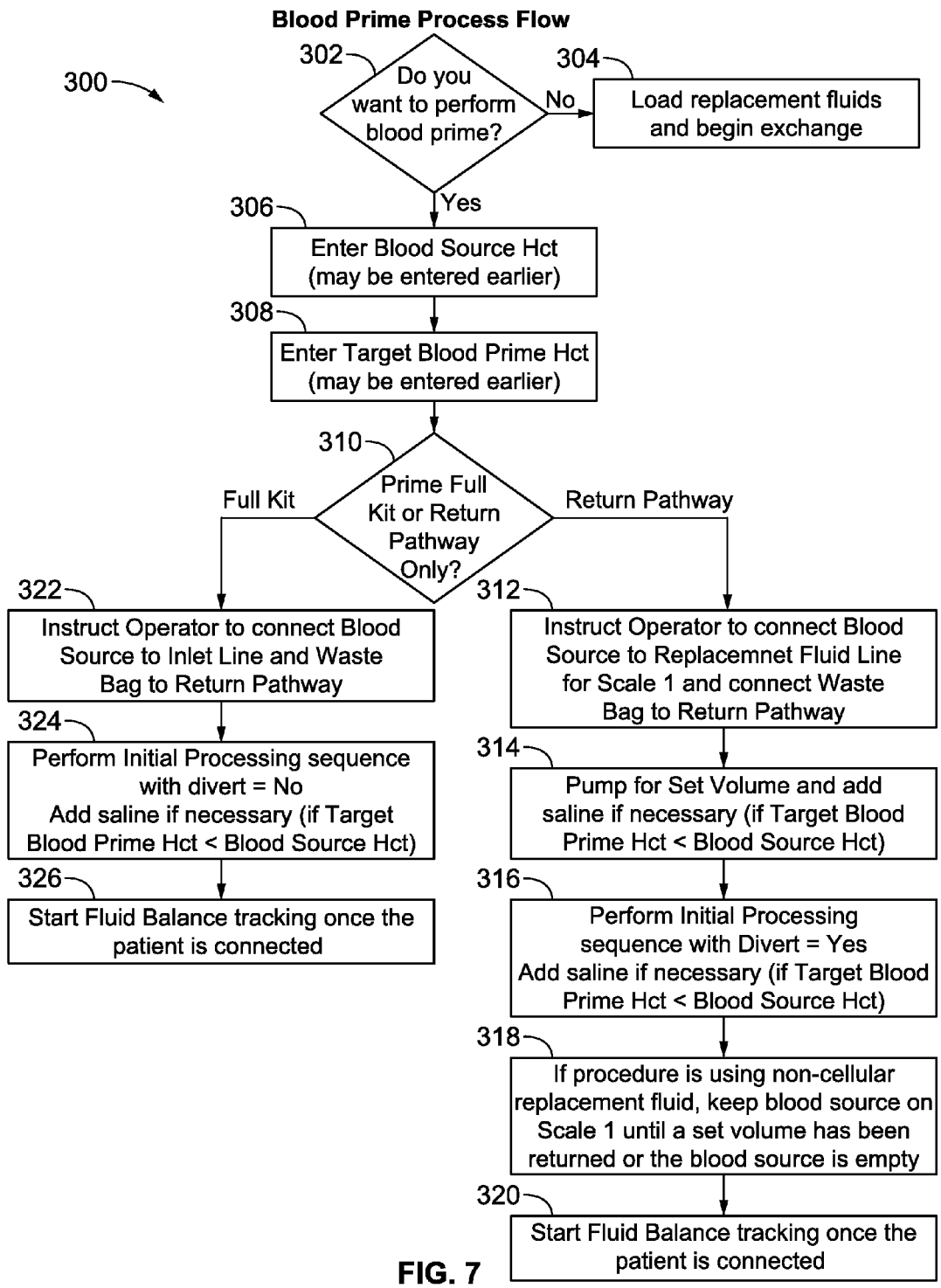
FIG. 7 is a flow chart setting forth a method for performing a blood prime in accordance with the present disclosure.

The various steps of the method are shown in FIG. 7. It should be understood that the flow chart of FIG. 7 is exemplary, and that one or more of the steps may be modified or omitted, according to the requirements of the operator and patient.

In broad terms, in accordance with the present disclosure, a method is provided for performing a blood prime that allows the operator the option of priming the entire disposable kit or just a portion of the kit, such as the return pathway. In addition to the type of blood prime, the operator will enter in the hematocrit of the blood or blood product being used for blood prime and the desired hematocrit for the blood prime. For priming the disposable kit with blood, the blood source will be attached to the inlet line of the disposable kit and the return line is connected to a waste container. The blood source may be ABO compatible whole blood or packed red blood cells, and a desired volume will be pumped from the blood source. If necessary, saline is added to the blood as it is drawn into the kit to achieve the desired blood prime hematocrit. The operator may elect to pump additional volume if desired.

If the option of priming just the return pathway is selected, the blood source is connected to the replacement fluid line 214A (FIGS. 3 and 4) and the return line connected to a waste container, e.g., 174B. A set volume is pumped from the blood source. The operator may elect to pump additional volume if desired.

If only the return pathway is primed with blood during blood prime, the system can automatically divert the saline from the saline prime remaining in the kit to the waste container 174B once the patient is connected and blood is being drawn from the patient. The system can also automatically deliver replacement fluid to the patient once blood is being drawn from the patient to maintain isovolemia and red blood cell volume. If the replacement fluid for the therapeutic procedure does not contain red cells (for example, in a therapeutic plasma exchange, where the replacement fluid is non-cellular, such as albumin), the operator can keep the blood prime fluid connected as replacement fluid until the disposable kit is filled with the patient's blood. If the operator keeps the blood prime source attached to the replacement fluid line and does not replace it with albumin, then the patient receives red blood cells during the initial processing state, when blood is first being withdrawn from the patient. Once the operator no longer observes saline exiting the separation chamber, this could indicate that the disposable kit is now filled with blood. The operator can then change the container on the replacement fluid line to albumin, and proceed with the plasma exchange. If the procedure uses a non-cellular replacement fluid, the blood source 170A will be maintained on scale 1 until a set volume has been returned or the source 170A is empty.

The user interface can provide instructions on what should be connected to the inlet, return and replacement fluid lines during the blood prime. It can also notify the operator of the appropriate time to disconnect the blood prime fluid. Inasmuch as the system knows which type of blood prime was selected, it can also account for the blood prime in its fluid balance calculations so the operator does not have to manually calculate fluid balance.

Turning to FIG. 7, a flow chart illustrating the various steps of a method 300 in accordance with the present disclosure is seen. The steps comprising the blood prime method are performed after the entire kit is primed with saline. The controller, through the user interface, may then provide a prompt to the operator as to whether a blood prime is to be performed (Box 302). If the operator indicates that no blood prime will be performed, the operator may then load and connect the replacement fluids to the kit and begin the exchange procedure (Box 304).

If the operator enters into the graphical user interface that a blood prime is to be performed, the operator receives a prompt seeking entry of the hematocrit value of the blood or blood product that will be used for performing the prime (Box 306), if this information has not already been preset by the operator prior to the start of the procedure. Typically, the blood or blood product used for priming is the same as the blood component that is to be replaced pursuant to the exchange procedure (e.g., red blood cells). As such, its hematocrit value may have been entered into the controller prior to generating the prompt as to whether to perform a blood prime without departing from the method.

The controller, through the user interface will also request input of a target hematocrit for the fluid comprising the blood prime when in the kit (Box 308). Typically, this target blood prime hematocrit is substantially the same as the hematocrit of the patient's blood so that, upon commencement of the therapeutic exchange procedure, the return of the fluid comprising the blood prime to the patient will maintain the patient's hematocrit level. The target hematocrit may have been entered at an earlier stage of the procedure, without departing from the method.

The user interface will then prompt the operator to indicate whether the full kit or a portion of the kit, typically the return pathway, is to be primed with blood (Box 310). In the context of the red blood cell exchange procedure, the decision as to whether to prime the entire kit or just a portion thereof is typically a matter of physician preference, and the operator will receive a direction from the physician on this. For procedures other than a red blood cell exchange procedure, the entire kit is typically primed with blood, as a red blood cell exchange is the only therapeutic procedure in which red blood cells are used as the replacement fluid.

Figure 3:
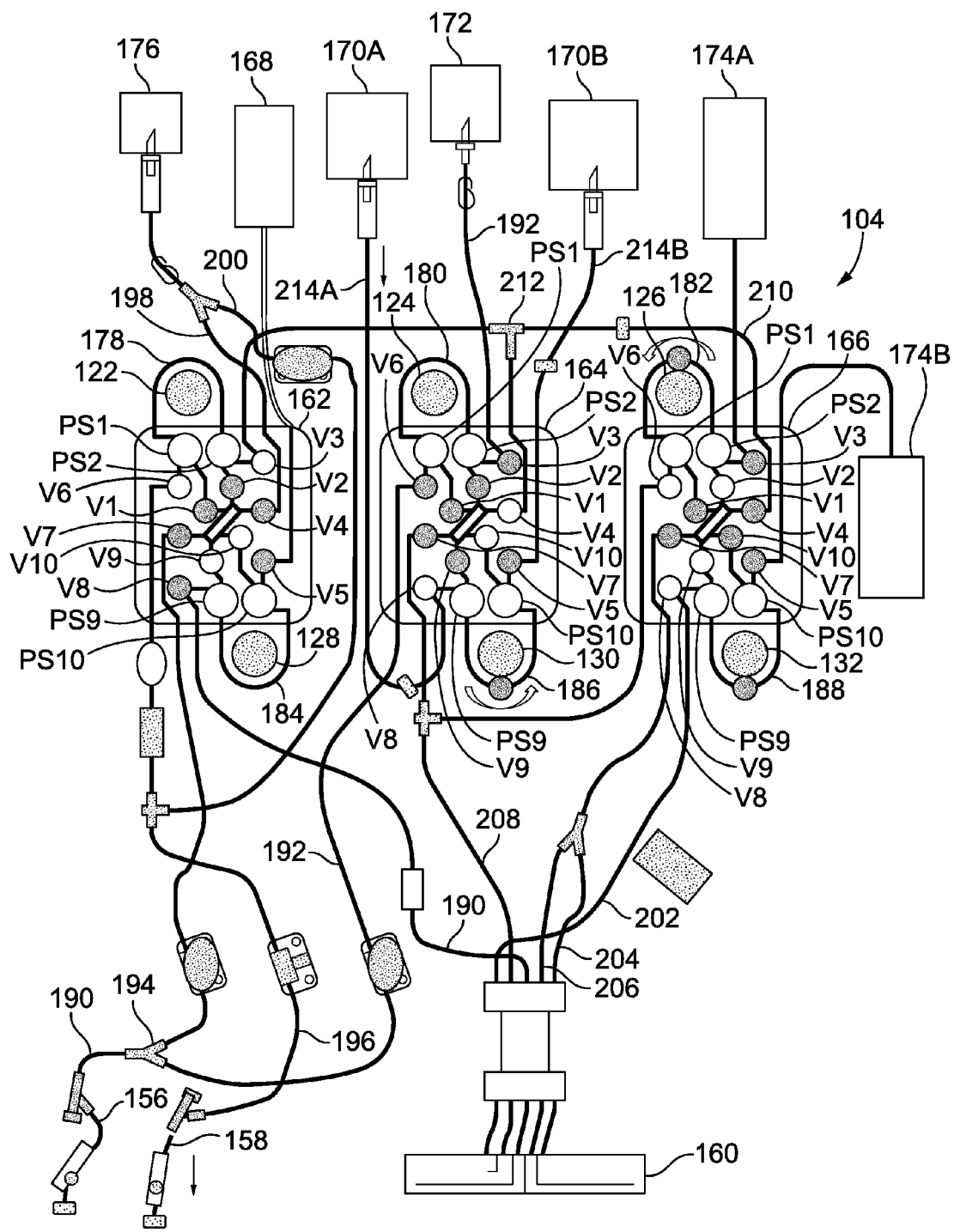
FIGS. 3-6 are plan views of a disposable tubing flow set for use with the processing device shown in FIG. 2, illustrating different modes of operation during a partial kit blood prime procedure (FIGS. 3 and 4) and a full kit blood prime procedure (FIGS. 5 and 6) in accordance with the present disclosure.
Figure 4:
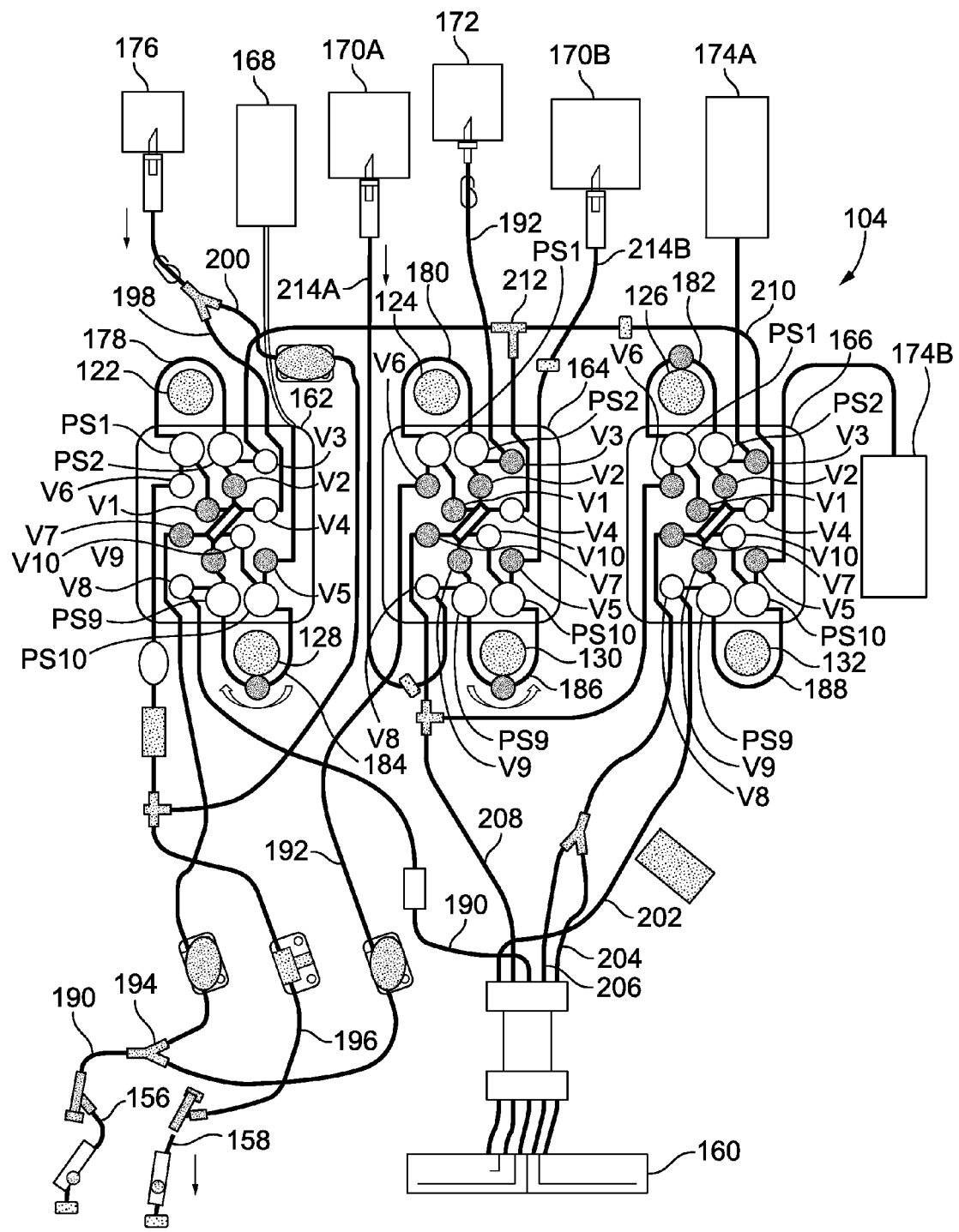

If the return pathway only is to be primed, the user interface will instruct the operator to connect the blood source through the replacement fluid line 214a for scale 1 170A and connect a waste bag to the return line (Box 312). The system then operates with the pumps, valves and pressure sensing chambers as shown in FIG. 3 to draw blood from blood source 170A by means of pump 130. If the hematocrit level of the blood used for the blood prime needs to be reduced, then saline from source 176 is added by means of the operation of pump 128 (Box 314) through the umbilicus portion of the kit, as shown in FIG. 4.

Pursuant to a prompt from the controller, the operator will be asked to indicate whether the saline prime in the inlet line is to be diverted and, if the operator indicates "yes", the saline prime in the inlet line and centrifuge chamber is routed to the waste bags and the blood prime is returned to the patient (Box 316).

During the blood prime, the pump 130 will pump for a set volume (substantially the volume of the return pathway that is being primed with blood).

Once the blood prime of the return line is complete, the controller will so indicate and prompt the operator to connect the patient to the inlet line 190 and return line 196 of the kit. The therapeutic procedure is then commenced with the fluid balance tracking started and accounting only for the volume of the blood drawn from and sent to the patient.

Figure 5:
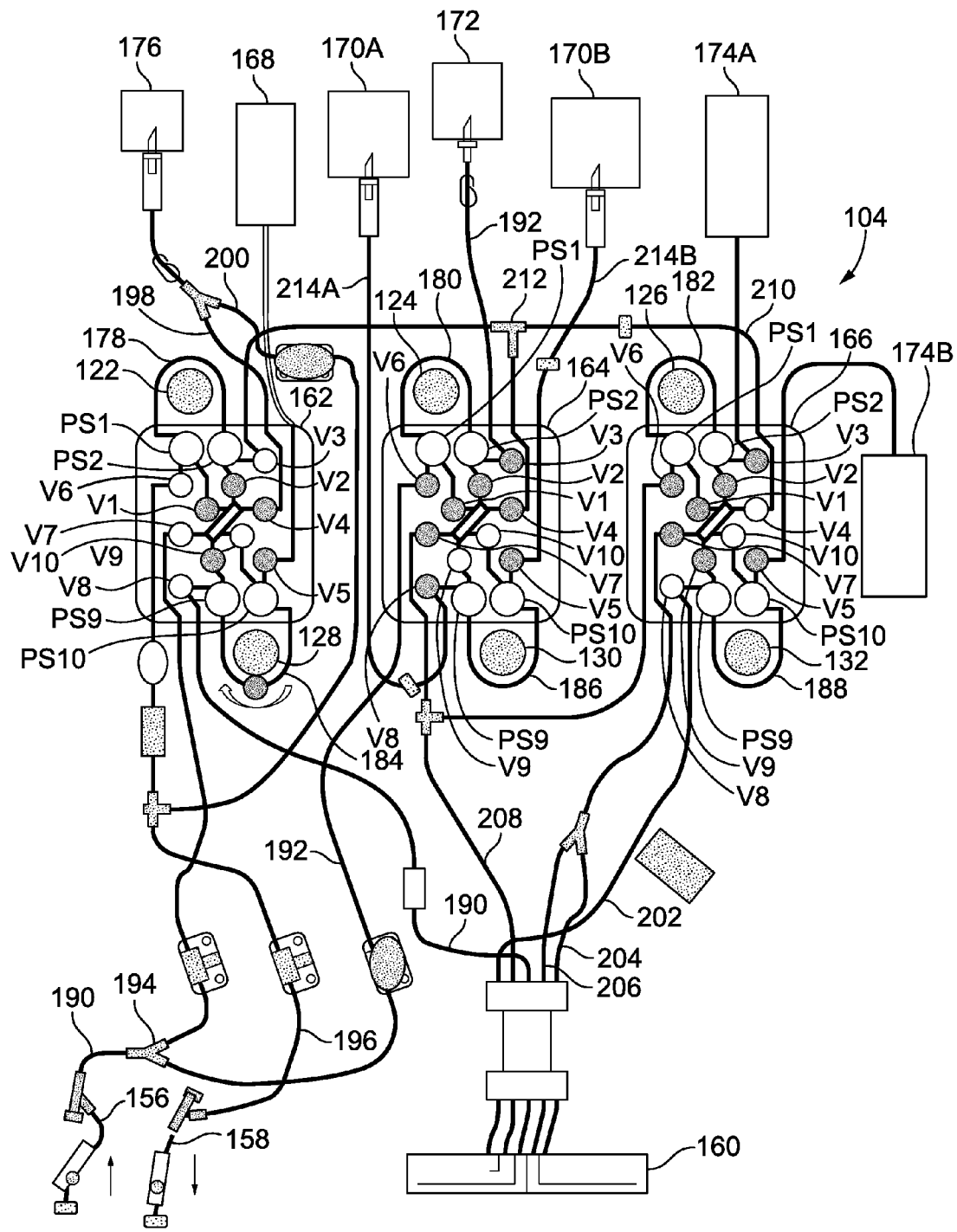
Figure 6:
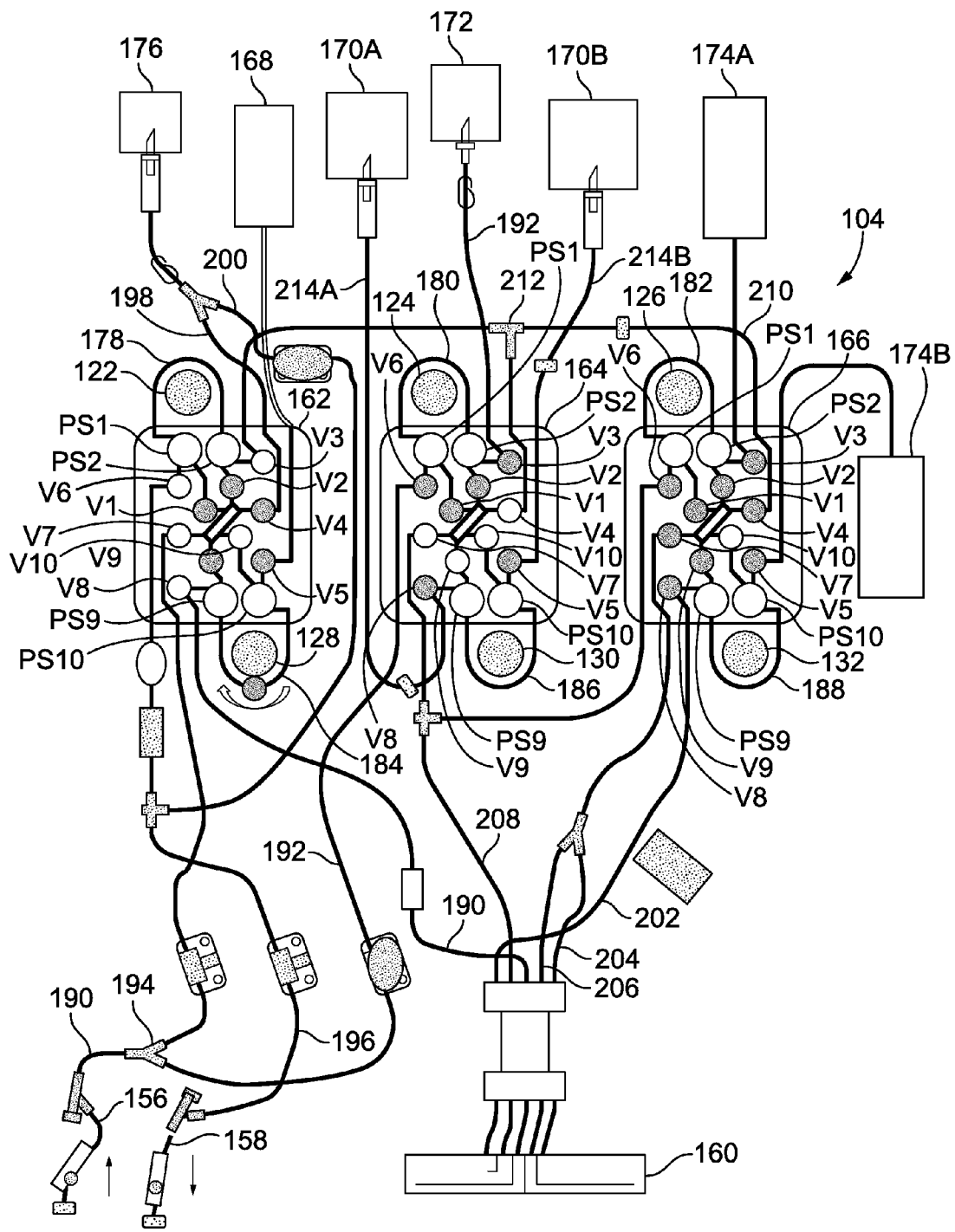

If, in response to the prompt regarding whether the full kit or the return pathway should be primed (Box 310), "full kit" is selected by the operator, the interface will then instruct the operator to connect the blood source for the blood prime to the inlet line 156 and a waste bag to the return line 158 (Box 322). The system then operates with the pumps, valves, and pressure sensors configured as shown in FIG. 5 for the first stage of the priming procedure and then as shown in FIG. 6 for the second stage. Again, as with the priming of the return pathway only, saline will be added to the blood used for priming if the target hematocrit of the fluid within the kit after performing the blood prime is less than the hematocrit of the blood source used for priming.

Once the entire kit is primed with blood, the controller will so indicate and prompt the operator to connect the patient to the kit. Once the therapeutic exchange is commenced, the system will begin tracking the fluid balance, thus taking into account only the volume of the blood that is drawn from and sent to the patient.

If the exchange procedure is a red blood cell exchange procedure, the procedure may now commence as is known to those skilled in the art. In this regard, systems and methods for achieving a target end hematocrit and a fluid balance during a therapeutic red blood cell exchange procedure are disclosed in U.S. Provisional Application Ser. No. 61/622,113, filed Apr. 10, 2012, and incorporated herein by reference.

Thus, this can be seen from the above description, the present disclosure has several different aspects which are not limited to the specific methods shown in the attached drawings or described above. Variations of these concepts may be embodied in other steps for carrying out the methods without departing from the scope of the disclosure.

The invention claimed is:

1. In a therapeutic procedure in which a selected blood component is separated from a patient's whole blood, and replaced with a previously-collected blood component, the procedure utilizing a durable separation device comprising a programmable controller including a user interface and a single-use kit, the kit comprising an inlet line, a separation chamber, and a return pathway, a method for priming at least a portion of the kit with previously-collected blood or blood product prior to flowing the patient's whole blood into the inlet line of the kit, the method comprising:
   entering into the controller a hematocrit value of the previously-collected blood or blood product;
   entering into the controller in response to a prompt by the controller a target hematocrit value for the previously-collected blood or blood product when residing in the kit;
   entering into the controller in response to a prompt by the controller an identification of the portion of the kit to be primed with the previously-collected blood or blood product;
   priming the identified portion of the kit by automatically introducing a selected amount of said previously-collected blood or blood product into said identified portion;
   connecting the patient to the inlet line and return pathway of the kit in response to a prompt from the controller after completion of the selected priming; and commencing with the therapeutic procedure, comprising tracking fluid balance of the patient accounting only for the volume drawn from and returned to the patient.

2. The method of claim 1 wherein the portion of the kit to be primed is either the entire kit or the return pathway.

3. The method of claim 2 further comprising connecting a source of previously-collected blood or blood product to the inlet line of the kit and a waste bag to the return pathway in response to a prompt by the controller after selecting priming the entire kit.

4. The method of claim 2 in which the entire kit is primed with saline prior to priming either the entire kit or the return pathway with the previously-collected blood or blood product.

5. The method of claim 2 further comprising connecting a source of the previously-collected blood or blood product to a replacement fluid line and a waste bag to the return pathway in response to a prompt by the controller after selecting priming the return line; measuring the amount of the source of the previously-collected blood or blood product; and diverting fluid displaced by the priming of the return line to the waste bag.

6. The method of claim 2 further comprising determining a hematocrit value for the whole blood of the patient and entering into the controller that hematocrit value for the target hematocrit value, and adding saline to the previously-collected blood or blood product during priming in an amount sufficient to attain the target hematocrit, if the target hematocrit value is less than the hematocrit of the previously-collected blood or blood product.

7. The method of claim 5 further comprising determining a hematocrit value for the whole blood of the patient and entering into the controller that hematocrit value for the target hematocrit value, and adding saline to the previously-collected blood or blood product during priming in an amount sufficient to attain the target hematocrit, if the target hematocrit value is less than the hematocrit of the previously-collected blood or blood product.

8. The method of claim 6 wherein the hematocrit value of the previously-collected blood or blood product is entered into the controller in response to a prompt by the controller.

9. The method of claim 7 wherein the hematocrit value of the previously-collected blood or blood product is entered into the controller in response to a prompt by the controller.

10. In a therapeutic procedure in which a selected blood component is separated from a patient's whole blood, and replaced with a previously-collected blood component, the procedure utilizing a durable separation device comprising a programmable controller including a user interface and a single-use kit, the kit comprising an inlet line, a separation chamber, and a return pathway, a method for priming at least a portion of the kit with previously-collected blood or blood product prior to flowing the patient's whole blood into the inlet line of the kit, the method comprising:
   priming the entire kit with saline;
   entering into the controller a hematocrit value of the previously-collected blood or blood product;
   entering into the controller in response to a prompt by the controller a target hematocrit value for the previously-collected blood or blood product when residing in the kit;
   determining a hematocrit value for the whole blood of the patient and entering into the controller that hematocrit value for the target hematocrit value, and adding saline to the previously-collected blood or blood product during priming in an amount sufficient to attain the target hematocrit, if the target hematocrit value is less than the hematocrit of the previously-collected blood or blood product;
   entering into the controller in response to a prompt by the controller an identification of the portion of the kit to be primed with the previously-collected blood or blood product as either the entire kit or the return pathway;
   priming the identified portion of the kit by automatically introducing a selected amount of said previously-collected blood or blood product into said identified portion;
   connecting the patient to the inlet line and return pathway of the kit in response to a prompt from the controller after completion of the selected priming; and
   commencing with the therapeutic procedure, comprising tracking fluid balance of the patient accounting only for the volume drawn from and returned to the patient.

11. A system for performing a procedure in which a selected blood component is separated from whole blood, the system comprising:
   a durable separation device comprising a plurality of flow control devices and a programmable controller, the controller programmed to perform a procedure in accordance with claim 1; and
   a single-use fluid processing kit comprising a plurality of flow paths, the fluid processing kit being mounted to the durable separation device.

12. A system for performing a procedure in which a selected blood component is separated from whole blood, the system comprising:
   a durable separation device comprising a plurality of flow control devices and a programmable controller, the controller programmed to perform a procedure in accordance with claim 10; and
   a single-use fluid processing kit comprising a plurality of flow paths, the fluid processing kit being mounted to the durable separation device.

13. The method of claim 10 further comprising connecting a source of previously-collected blood or blood product to the inlet line of the kit and a waste bag to the return pathway in response to a prompt by the controller after selecting priming the entire kit.

14. The method of claim 10 further comprising connecting a source of the previously-collected blood or blood product to a replacement fluid line and a waste bag to the return pathway in response to a prompt by the controller after selecting priming the return line; measuring the amount of the source of the previously-collected blood or blood product; and diverting fluid displaced by the priming of the return line to the waste bag.

15. The method of claim 10 wherein the hematocrit value of the previously- collected blood or blood product is entered into the controller in response to a prompt by the controller.

16. The system of claim 11 wherein the controller is further programmed to provide a prompt for connecting a source of previously-collected blood or blood product to the inlet line of the kit and a waste bag to the return after selection of priming the entire kit.

17. The system of claim 11 wherein the controller is further programmed to provide a prompt for connecting a source of the previously-collected blood or blood product to a replacement fluid line and a waste bag to the return pathway after selection of priming the return line.

18. The system of claim 11 wherein the controller is further programmed to provide a prompt for entering the hematocrit value of the previously-collected blood or blood product.

19. The system of claim 12 wherein the controller is further programmed to provide a prompt for connecting a source of previously-collected blood or blood product to the inlet line of the kit and a waste bag to the return after selection of priming the entire kit.

20. The system of claim 12 wherein the controller is further programmed to provide a prompt for connecting a source of the previously-collected blood or blood product to a replacement fluid line and a waste bag to the return pathway after selection of priming the return line.

\* \* \* \* \*